| United States Patent [19] | [11] Patent Number: 4,762,849 |
| Grisar et al. | [45] Date of Patent: Aug. 9, 1988 |

[54] CARDIOTONIC ALKANOYLTHIAZOLONES

[75] Inventors: J. Martin Grisar, Wissembourg, France; Richard C. Dage; Richard A. Schnettler, both of Cincinnati, Ohio

[73] Assignee: Merrell Dow Pharmaceuticals Inc., Cincinnati, Ohio

[21] Appl. No.: 787,276

[22] Filed: Oct. 15, 1985

[51] Int. Cl.$^4$ .................. C07D 277/34; A61K 31/425
[52] U.S. Cl. .................................... 514/369; 548/188
[58] Field of Search ........................ 548/188; 514/369

[56] References Cited

U.S. PATENT DOCUMENTS

| 3,514,465 | 5/1970 | Posselt et al. | 548/183 |
| 3,948,925 | 4/1976 | Perronnet et al. | 548/187 |
| 4,405,635 | 9/1983 | Schnettler | 548/317 |
| 4,405,638 | 9/1983 | Cavazza | 549/71 |
| 4,623,651 | 11/1986 | Grisar et al. | |

FOREIGN PATENT DOCUMENTS 0117082 8/1984 European Pat. Off. .

OTHER PUBLICATIONS

Y. Yamamoto, *J. Pharm. Soc. Japan* 72, 1020, (1952), Abstracted at Chemical Abstracts, vol. 46, cols. 10285–10286.

R. A. Schnettler, 4–Substituted–1,3–Dihydro–2-H–Imidazol-2-ones, 187th American Chemical Society National Meeting, Apr. 8–13, 1984.

E. Ochiai, *J. Pharm. Soc. Japan*, 60, 164, (1940), Abstracted at Chemical Abstracts, vol. 34, cols. 3449–3450.

*Primary Examiner*—Robert Gerstl
*Attorney, Agent, or Firm*—Raymond A. McDonald

[57] ABSTRACT

Novel alkanoylthiazolones enhance myocardial contractile force and are useful as cardiotonics in the treatment of heart failure.

17 Claims, No Drawings

CARDIOTONIC ALKANOYLTHIAZOLONES

BACKGROUND OF THE INVENTION

This invention relates to certain alkanoylthiazolones, their use to enhance myocardial contractile force, and their use as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and high-output and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea and pulmonary edema.

Treatment involves either removal or correction of the underlying cause or involves control of the heart failure state. Management or control can be accomplished by increasing cardiac output or by decreasing cardiac work load. While work load can be reduced by reduction of physical activities and physical and emotional rest, increasing cardiac output has traditionally involved digitalis therapy. Digitalis stimulates contractile force of the heart which increases cardiac output and improves ventricular emptying. In this way, digitalis therapy normalizes venous pressure and reduces peripheral vasoconstriction, circulatory congestion, and organ hypoperfusion.

Unfortunately, optimal doses of digitalis vary with the patient's age, size and condition and the therapeutic to toxic ratio is quite narrow. In most patients the lethal dose is only about five to ten times the minimal effective dose with toxic effects becoming apparent at only 1.5-2.0 times the effective dose. For these reasons, dose must be carefully tailored to suit the individual patient and frequent clinical examinations and electrocardiograms are necessary to detect early signs of digitalis intoxication. Despite this care digitalis intoxication is reported in up to one-fifth of hospitalized patients undergoing therapy.

The need for less toxic cardiotonic agents is readily apparent. Applicants have discovered certain alkanoylthiazolones which possess potent cardiotoxic activity and by comparison to digitalis have fewer toxic effects.

SUMMARY OF THE INVENTION

This invention is directed to pharmaceutically active alkanoylthiazolones of formula 1

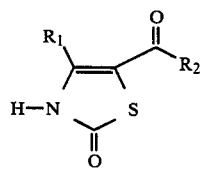

wherein
$R_1$ is a hydrogen or $(C_1-C_4)$ alkyl group, and
$R_2$ is a $(C_1-C_6)$alkyl, $(C_2-C_6)$alkenyl, $(C_2-C_6)$alkynyl, $(C_3-C_7)$cycloalkyl, or $(C_3-C_7)$cycloalkyl$(C_1-C_6)$alkyl group.

These compounds enhance myocardial contractile force and are useful as cardiotonic agents in the treatment of heart failure.

DETAILED DESCRIPTION OF THE INVENTION

The formula 1 compounds exist in two tautomeric forms structurally depicted in formula 2

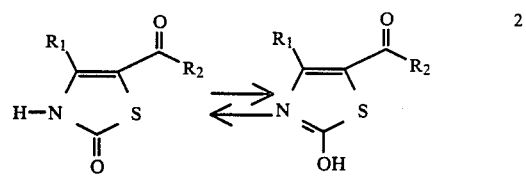

wherein $R_1$ and $R_2$ are as defined above. Throughout this disclosure, alkanoylthiazolones of formula 1 are intended to include the tautomers of formula 2.

The ring nitrogen of the formula 1 compounds can be substituted with a $(C_1-C_6)$ alkyl group, an alkanoyl group such as an acetyl group, or a benzoyl group. These nitrogen substituted compounds are equivalent to the unsubstituted compounds primarily because the substituent is lost upon administration to a patient, but also because many of the nitrogen substituted compounds independently possess significant ability to enhance myocardial contractile force and are useful cardiotonic agents.

As used herein, the term $(C_1-C_6)$ alkyl group means a straight or branched alkyl group of from one to six carbon atoms. Illustrative examples of a $(C_1-C_6)$alkyl group are methyl, ethyl, isopropyl, sec-butyl, pentyl, 3-methylbutyl, and 4-methylpentyl. The term $(C_1-C_4)$alkyl means a straight or branched alkyl group of from one to four carbon atoms.

The term $(C_2-C_6)$ group means a straight or branched alkenyl group of from two to six carbon atoms. The alkenyl groups of this invention can have one or two olefinic bonds. Illustrative examples of $(C_2-C_6)$ alkenyl groups are ethenyl, 1-methylethenyl, 2-propenyl, 1-methyl-2-propenyl, 2-butenyl, 1-methyl-2-butenyl, 2,4-hexadienyl, and 1-methyl-2,4-pentadienyl.

The term $(C_2-C_6)$ means a straight or branched alkynyl having from two to six carbon atoms and one or two triple bonds such as 2-propynyl, 1-methyl-2-propynyl, 2- (butynyl, 1-methyl-2-butynyl, and 2,4-hexadiynyl.

The term $(C_3-C_7)$ cycloalkyl means cyclopropyl, cyclobutyl, cyclopentyl, cyclohexyl and cycloheptyl. The term $(C_3-C_7)$ cycloalkyl $(C_{1-C_6})$ alkyl means those $(C_{l-C_6})$ alkyl groups substituted with a $(C_3-C_7)$cycloalkyl group. Examples of $(C_3-C_7)$ cycloalkyl $(C_1-C_6)$ alkyl groups are cyclohexylmethy 2-cyclopropyl-2-methylethyl, 44-cyclopentylbutyl and cyclopentylmethyl.

Preferred compounds of this invention are those compounds of formula 1 wherein $R_1$ is a hydrogen, methyl, or ethyl group. Also preferred are those formula 1 compounds wherein $R_2$ is a $(C_1-C_6)$ alkyl group. More preferred are those compounds of formula 1 wherein $R_2$ is a methyl, ethyl, or propyl group. Most preferred are those compounds wherein $R_1$ is a methyl group and wherein $R_2$ is an ethyl group.

As examples of compounds of formula 1 there can be mentioned the following:
4-methyl-5-propionyl-2(3H)-thiazolone;
5-(3-methylbutyryl)-2(3H)-thiazolone;

5-acryloyl-4-ethyl-2(3H)-thiazolone;
5-crotonyl-4-propyl-2(3H)-thiazolone;
5-(1-oxo-2,4-hexadienyl)-4-sec-butyl-2(3H)-thiazolone;
4-isopropyl-5-(1-oxo-2-propynyl)-2(3H)-thiazolone;
4-cyclohexylcarbonyl-2(3H)-thiazolone; and
5-(4-cyclopentylbutanoyl)-4-methyl-2(3 H)-thiazolone.

The formula 1 compounds can be prepared in any manner by standard techniques analogously known by those skilled in the art. For example the formula 1 compounds can be prepared by a Friedel-Crafts acylation of a thiazolone of formula 3

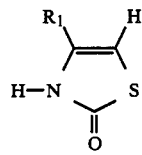

wherein $R_1$ is as defined above. The acylating reagent can be an acid halide of formula 4

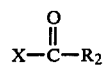

wherein $R_2$ is as defined above and X is a bromo group or preferably a chloro group. In addition the acylating reagent of the Friedel-Crafts reaction can be the free acid or acid anhydride corresponding to the formula 4 acid halide. Mixed acid anhydrides may also be utilized. The Friedel-Crafts reaction is well known to those skilled in the art and has been reviewed by P. H. Gore in "Friedel-Crafts and Related Reactions", G. A. Olah, editor, Vol. III, Part 1, Interscience Publications, New York, 1964.

The Friedel-Crafts reaction is performed by premixing about 1 molar equivalent of the appropriate thiazolone of formula 3 with about 1 molar equivalent to about 10 molar equivalents, preferably about 2 to 3 molar equivalents, of a Lewis acid catalyst in a suitable solvent, for example, petroleum ethers; a chlorinated aromatic, such as 1,2,4-trichlorobenzene or o-dichlorobenzene; carbon disulfide; nitrobenzene; or a chlorinated hydrocarbon such as carbon tetrachloride, ethylene chloride, methylene chloride, chloroform or preferably tetrachloroethane. About 1 molar equivalent to about 10 molar equivalents, preferably about 2 molar equivalents, of the appropriate acid halide of formula 4 is added, preferably dropwise, to the mixture of thiazolone, Lewis acid, and solvent and the reaction is allowed to proceed for about ½ hour to about 100 hours, preferably from about 1 hour to about 10 hours depending on the reactants, the solvent, and the temperature which can be from about −78° to about 150° C., preferably about 0° to about 100° C., most preferably about 60–100° C. The resulting alkanoyl thiazolone may be isolated from the reaction mixture by any suitable art-known procedure, preferably by quenching the reaction mixture with ice water and subsequently removing the product by filtration or extraction and solvent removal or by quenching the cooled reaction mixture with hydrochloric acid and subsequently collecting the solid product by filtration. Purification can be accomplished by, for example, recrystallization, preferably from ethanol.

Lewis acid catalysts suitable for use in the Friedel-Crafts reactions described herein are, for example, a metal, such as aluminum, cerium, copper, iron, molybenum, tungsten or zinc; a Bronstead acid, such as a phosphoric acid, sulfuric acid, sulfonic acid, or a hydrohalic acid, such as hydrochloric or hydrobromic acid; halogen substituted acetic acids, such as chloroacetic or trifluoroacetic acids; or a metallic halide, such as a boron halide, zinc chloride, zinc bromide, berryl chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

The thiazolones of formula 3 are generally available or can be readily prepared by standard laboratory procedures. For example 4-methyl-2(3H)-thiazolone is prepared by reaction of chloroacetone and potassium thiocyanate in the presence of aqueous sodium bicarbonate by the procedure of Tcherniac, J. Chem. Soc., 115, 1071 (1919).

The compounds of formula 1 are cardiotonic agents useful in the treatment of heart failure. These compounds can also be used in the treatment of any other condition requiring enhanced myocardial contractile force.

The utility of formula 1 compounds as cardiotonics may be determined by administering the test compound (0.1–100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of 0.25-2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severly depressed. Reversal of these effects by the test compound indicates cardiotonic activity.

The compounds may be administered in various manners to achieve the desired effect. The compounds may be administered alone or in the form of pharmaceutical preparations to the patient being treated either topically, orally or parenterally, that is, intravenously or intramuscularly. The amount of compound administered will vary with the patient, the severity of the cardiac failure and the mode of administration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferably about 15 to 235 mg of the active ingredient. For parenteral administration a unit dosage may contain, for example, from 5 to 700 mg of the active ingredient, preferably about 15 to 21 mg. Repetitive daily administration of the compounds may be desired and will vary with the condition of the patient and the mode of administration.

As used herein, the term "patient" is taken to mean warm blooded animals, for example, birds, such as chickens and turkeys, and mammals, such as sheep, horses, bovine cows and bulls, pigs, dogs, cats, rats, mice and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and an inert filler, such as lactose, sucrose or cornstarch. In another embodiment the compounds of general formula 1 can be tableted with conventional tablet bases such as lactose, sucrose or cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils, and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

The following specific examples further illustrate the preparation and use of the compounds of formula 1 but are not intended to limit the scope of the invention.

EXAMPLE 1

4-Methyl-5-(1-Oxopropyl)-2(3H)-Thiazolone

4-Methyl-2(3H)-thiazolone (5.8 g, 0.05 mol) and propionyl chloride (9.2 g, 0.1 mol) were added to a slurry of aluminum chloride (20.0 g, 0.15 mol) in tetrachloroethane (120 ml). The mixture was stirred for 4 hours at 70° C. and for 2 hours at 90° C. After cooling, 2N hydrochloric acid (150 ml) was added dropwise. The resulting precipitate was collected, washed with water, then dichloromethane, and recrystallized twice from ethanol to give the purified title compound, m.p. 163–165° C.

In a like manner but substituting butyryl chloride, tert-butylacetyl chloride, cyclopropanecarboxylic acid chloride crotonyl chloride, or cyclohexanecarboxylic acid chloride for the propionyl chloride in the above example, results in 4-methyl-5-(1-oxobutyl)-2(3H)-thiazolone,
4-methyl-5-(1-oxo-3,3-dimethylbutyl)-2(3H)-thiazolone,
4methyl-5-(1-oxo-1-cyclopropylmethyl)-2(3H)-thiazolone,
4-methyl-5-crotonyl-2(3H)-thiazolone, or
4-methyl-5-(1-oxo-1-cyclohexylmethyl)-2(3H)-thiazolone.

EXAMPLE 2

A tablet is prepared from

| | |
|---|---|
| 4-methyl-5-propionyl-2(3H)—thiazolone | 250 mg |
| starch | 40 mg |
| talc | 10 mg |
| magnesium stearate | 10 mg |

EXAMPLE 3

| | |
|---|---|
| 4-acetyl-2(3H)—thiazolone | 400 mg |
| talc | 40 mg |
| sodium carboxymethylcellulose | 40 mg |
| starch | 120 mg |

We claim:
1. An alkanoylthiazolone of the formula

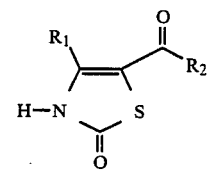

wherein $R_1$ is a hydrogen or $(C_1-C_4)$alkyl group and $R_2$ is a $(C_2-C_6)$ alkenyl, $(C_2-C_6)$alkynyl, $(C_3-C_6)$cycloalkyl, or $(C_3-C_7)$cycloalkyl $(C_1-C_6)$ 2. An alkanoylthiazolone of claim 1 wherein $R_1$ is a hydrogen, methyl, or ethyl group.

3. An alkanoylthiazolone of claim 1 wherein $R_1$ is a methyl group.

4. A method of treating heart failure in a patient in need thereof which comprises administering to the patient a cardiotonically effective amount of an alkanoylthiazolone of the formula

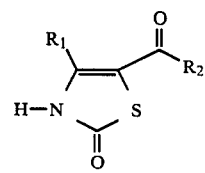

wherein $R_1$ is a hydrogen or $(C_1-C_4)$ alkyl group and $R_2$ is a $(C_1-C_6)$alkyl, $(C_2-C_6)$alkenyl, $(C_2-C_6)$ alkynyl, $(C_3-C_7)$cycloalkyl, or $(C_3-C_7)$cycloalkyl $(C_1-C_6)$alklyl group.

5. A method of claim 4 wherein $R_2$ is a $(C_1-C_6)$alkyl group.

6. A method of claim 5 wherein $R_1$ is a hydrogen, methyl, or ethyl group.

7. A method of claim 4 wherein $R_2$ is a methyl, ethyl, or propyl group.

8. A method of claim 4 wherein $R_1$ is a hydrogen, methyl, or ethyl group.

9. A method of claim 4 wherein $R_2$ is an ethyl group.

10. A method of claim 4 wherein $R_1$ is a methyl group and $R_2$ is an ethyl group.

11. A method of enhancing mycardial contractile force in a patient in need thereof which comprises administering to the patient an effective amount of alkanoylthiazolone of the formula

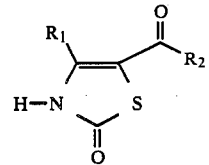

wherein $R_1$ is a hydrogen or $(C_1-C_4)$alkyl group and $R_2$ is a $(C_1-C_6)$alkyl, $(C_2-C_6)$alkenyl, $(C_2-C_6)$ alkynyl, $(C_3-C_7)$cycloalkyl, or $(C_3-C_7)$cycloalkyl $(C_1-C_6)$alkyl group.

12. A method of claim 11 wherein $R_2$ is a $(C_1-C_6)$alkyl group.

13. A method of claim 12 wherein $R_l$ is a hydrogen, methyl or ethyl group.

14. A method of claim 11 wherein $R_2$ is a methyl, ethyl, or propyl group.

15. A method of claim 14 wherein $R_l$ is a hydrogen, methyl, or ethyl group.

16. A method of claim 11 wherein $R_2$ is an ethyl group.

17. A method of claim 11 wherein $R_l$ is methyl group and $R_2$ is an ethyl group.

* * * * *

UNITED STATES PATENT AND TRADEMARK OFFICE
CERTIFICATE OF CORRECTION

PATENT NO. : 4,762,849
DATED : August 9, 1988
INVENTOR(S) : J.M. Grisar; R.C. Dage; R.A. Schnettler It is certified that error appears in the above-identified patent and that said Letters Patent is hereby corrected as shown below:

At Column 2, Line 38 the patent reads: "($C_2$-$C_6$) group" and should read --($C_2$-$C_6$) alkenyl group--.

At Column 2, Line 45 the patent reads: "($C_2$-$C_6$) means" and should read --($C_2$-$C_6$)alkynyl means--.

At Column 2, Line 54 the patent reads: "cyclohexylmethy" and should read --cyclohexylmethyl--.

At Column 2, Line 55 the patent reads: "44-cyclopentylbutyl" and should read --4-cyclopentylbutyl--.

At Column 3, Line 5 the patent reads: "4-cyclohexylcarbonyl" and should read --5-cyclohexylcarbonyl--.

At Column 4, Line 28 the patent reads: "intrag astrically" and should read --intragastrically--.

At Column 5, Line 60 the patent reads: "# 9.2 g, 0.1 mol)" and should read --(9.2 g, 0.1 mol)--.

At Column 6, Line 24 thru 25 the patent reads: "Example 3" and should read --Example 3
A capsule is prepared from--.

At Column 6, Line 44 the patent reads: "($C_3$-$C_6$) cycloalkyl" and should read --($C_3$-$C_7$)cycloalkyl--.

At Column 6, Line 45 the patent reads: "($C_1$-$C_6$)" and should read --($C_1$-$C_6$) alkyl group--.

UNITED STATES PATENT AND TRADEMARK OFFICE
CERTIFICATE OF CORRECTION

PATENT NO. : 4,762,849

DATED : August 9, 1988

INVENTOR(S) : J.M. Grisar; R.C. Dage; R.A. Schnettler    Page 2 of 2

It is certified that error appears in the above-identified patent and that said Letters Patent is hereby corrected as shown below:

At Column 6, Line 65 the patent reads "alklyl group" and should read --alkyl group--.

At Column 7, Line 20 the patent reads "mycardial" and should read --myocardial--.

At Column 7, Line 24 the patent reads "of alkanoyl" and should read --of an alkanoyl--.

Signed and Sealed this

Fourteenth Day of November, 1989

Attest:

JEFFREY M. SAMUELS

*Attesting Officer*    *Acting Commissioner of Patents and Trademarks*